United States Patent
Larson, III

[11] Patent Number: 5,906,618
[45] Date of Patent: May 25, 1999

[54] MICROCATHETER WITH AUXILIARY PARACHUTE GUIDE STRUCTURE

[75] Inventor: Theodore C. Larson, III, Nashville, Tenn.

[73] Assignee: Vanderbilt University, Nashville, Tenn.

[21] Appl. No.: 08/821,089

[22] Filed: Mar. 20, 1997

[51] Int. Cl.⁶ .................................................. A61F 11/00
[52] U.S. Cl. ......................................... 606/108; 606/127
[58] Field of Search ............................ 606/1, 108, 110, 606/113, 114, 127, 128, 151, 213

[56] References Cited

U.S. PATENT DOCUMENTS

| | | | |
|---|---|---|---|
| 3,472,230 | 10/1969 | Fogarty | 606/127 |
| 4,198,960 | 4/1980 | Utsugi | 606/127 |
| 4,418,688 | 12/1983 | Loeb . | |
| 4,551,132 | 11/1985 | Pasztor et al. | 604/52 |
| 4,790,812 | 12/1988 | Hawkins, Jr. et al. | 604/22 |
| 5,074,867 | 12/1991 | Wilk | 606/127 |
| 5,100,379 | 3/1992 | Wendell | 604/51 |
| 5,122,136 | 6/1992 | Guglielmi et al. . | |
| 5,275,173 | 1/1994 | Samson et al. | 128/772 |
| 5,336,205 | 8/1994 | Zenzen et al. | 604/280 |
| 5,354,295 | 10/1994 | Guglielmi et al. | 606/32 |
| 5,405,360 | 4/1995 | Tovey | 606/151 |
| 5,540,680 | 7/1996 | Guglielmi et al. | 606/32 |
| 5,643,317 | 7/1997 | Pavcnik et al. | 606/151 |

FOREIGN PATENT DOCUMENTS 2567405  7/1984  France .

*Primary Examiner*—Glenn K. Dawson
*Attorney, Agent, or Firm*—Waddey & Patterson; Mark J. Patterson

[57] ABSTRACT

A microcatheter with a deployable parachute attached to its distal tip is disclosed. The parachute in its retracted position lies flush against the exterior wall of the distal segment of the catheter. Control strings, cables or wires traverse the length of the microcatheter through channels within its wall and exit through strategically placed apertures at the tip of the microcatheter to attach to the parachute. When the parachute is deployed, the microcatheter is guided by blood flow or jets of liquid that are injected through the microcatheter. When the parachute is retracted, the microcatheter may be used with a guidewire to superselect vasculature. The microcatheter device has multiple uses permitting diagnostic and therapeutic superselective angiography.

14 Claims, 5 Drawing Sheets

MICROCATHETER WITH AUXILIARY PARACHUTE GUIDE STRUCTURE

BACKGROUND OF THE INVENTION

The present invention relates generally to microcatheters used in the field of interventional radiology. More particularly, this invention pertains to microcatheters used in endovascular procedures for diagnostic imaging and therapy of vascular pathology.

Since the 1980's, microcatheter technology has advanced to become commonplace in the treatment of vascular lesions of the central nervous system. Microcatheters have been used to treat cerebral aneurysms, fistulas, and arterial venous malformations, for example, by occluding the parent vessel or the pathologic vascular abnormality through an endovascular approach, using selective deposition of coils, particles, or liquid adhesives. The microcatheter can also be used to deliver chemotherapeutic agents to spinal, head and neck, or intracranial malignancies. Microcatheters are used as well to deliver agents to open occluded vasculature, including agents to dissolve clots. Balloon microcatheters are used to open vessels narrowed due to atherosclerosis.

As used in the prior art, a microcatheter is advanced from a femoral puncture through the lumen of a guiding catheter which terminates in a carotid or vertebral artery. The microcatheter is advanced beyond the guiding catheter using one of two known techniques. One such prior art technique is directing a guide wire through the lumen of the microcatheter which has varying degrees of tip-shape, torqueability, stiffness and external coating. A second prior art method is a flow-directed technique in which the microcatheter is extremely flexible and is carried by blood flow to the lesion, assisted by of injections of saline or contrast media through the flow directed microcatheter.

Each of the primary conventional methodologies for delivering a microcatheter has drawbacks. The guidewire directed microcatheter involves the risk of puncturing a vessel or aneurysm, which can have devastating hemorrhagic consequences intracranially. With the flow-directed microcatheter, it is frequently difficult to make precise turns and select individual vessels when complex vascular anatomy is encountered. A guidewire cannot be used in the flow-directed microcatheter because of the suppleness of the microcatheter and the significant possibilities of puncturing the wall of the microcatheter with a stiff guidewire. This also prohibits the delivery of coils (used to assist in occlusion) through a flow-directed microcatheter. Thus, only liquid adhesive or tiny particles can be injected through the flow-directed variety of microcatheter for vascular occlusion, the tiny particles usually of insufficient size to achieve the desired vascular occlusion. Conversely, the guide-wire directed microcatheter often times cannot be pushed from the groin over a guidewire through multiple turns in branching intracranial vascularity to reach the desired vessel.

In one prior art attempt at improvement of these techniques, a method has been developed to incorporate a balloon into the tip of a microcatheter to allow the blood flow to carry the distended balloon distally to the desired target vessel. The disadvantage with the balloon technology is that two lumens are required, one for the lumen to deliver the embolic agent, and the second to inflate and deflate the balloon. Alternatively, a calibrated leak balloon can be incorporated in the tip of the microcatheter. This, however, does not allow for directionality and cannot be used with a guidewire.

Thus, it is an object of the present invention to achieve catheterization of high-flow vascular lesions in the head, or elsewhere, using flow-directed as well as guidewire technology and permitting delivery of all embolic agents.

SUMMARY OF THE INVENTION

A microcatheter is provided with an auxiliary guide structure which is shaped and which functions like a parachute. The rectangular, trapezoid, or triangular parachute is joined to the catheter by proximal and distal control strings attached to the corners of the parachute. The control strings pass through distal and proximal apertures in the catheter wall and enter string channels formed in the catheter wall. The control strings then extend through the channels back to the proximal or hub end of the microcatheter where they again exit the catheter so that they can be manipulated by the radiologist. The distal control string apertures are proximate the catheter tip. The proximal control string apertures are spaced away from the distal apertures. The distal and proximal apertures are separated by a distance which is less than the diameter of the catheter.

The catheter is advanced through a guide catheter to the vasculature by retracting the control strings so that the parachute is positioned flat against the exterior wall of the catheter. The position of the microcatheter is tracked by radiographically monitoring a radio-opaque marker band around the catheter tip. The microcatheter is advanced to the target area using the parachute which is initially deployed by advancing the control strings distally. The catheter can then be further advanced by the action of blood or injected fluid flow against the parachute. Precision direction control is facilitated by manipulation of the distal and proximal control strings from the hub end of the microcatheter.

When the procedure is concluded, the parachute is retracted to its non-deployed position and the microcatheter is withdrawn.

BRIEF DESCRIPTION OF THE DRAWINGS

FIG. 7b is an enlarged plan view of the distal segment and tip of the microcatheter as shown in FIG. 7a.

FIG. 7c is an enlarged side view of the distal segment and tip of the microcatheter as shown in FIG. 7a.

FIG. 8b is an enlarged plan view of the distal segment and tip of the microcatheter as shown in FIG. 8a.

FIG. 8c is an enlarged side view of the distal segment and tip of the microcatheter as shown in FIG. 8a.

DESCRIPTION OF THE PREFERRED EMBODIMENTS

Figure 1A:
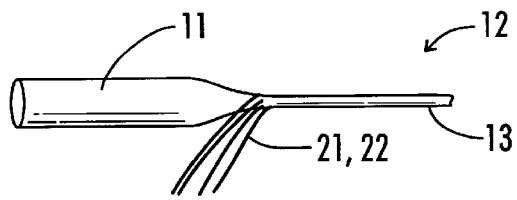
FIG. 1a is a side view of a first embodiment of the microcatheter of this invention, showing four control strings, cables, or wires exiting from the proximal segment of the microcatheter just before attachment to the plastic hub
Figure 8C:
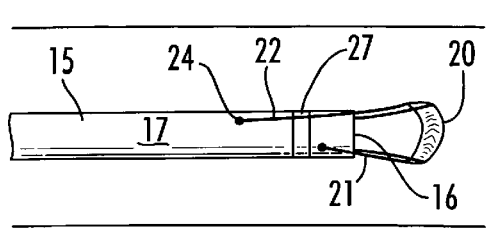
Figure 8B:
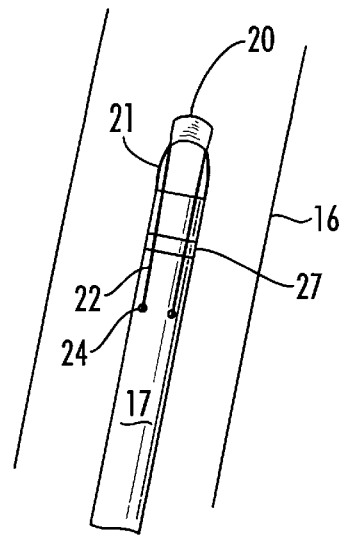
Figure 8A:
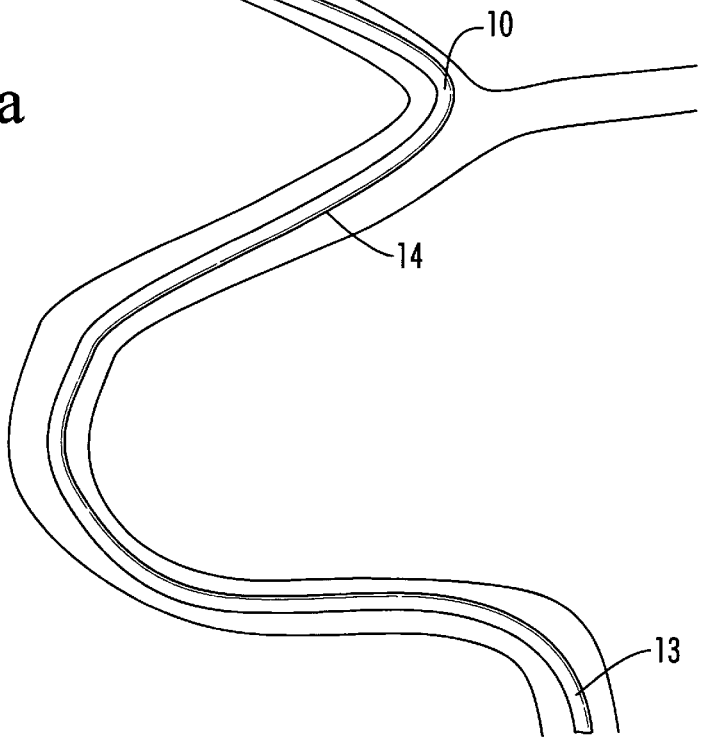
FIG. 8a is a plan view of the microcatheter of the present invention as it is guided through a vascular structure with the parachute in its deployed position.

Looking at FIGS. 1a and 8a, the microcatheter 10 has a hub portion 11 joined to catheter portion 12. In its preferred embodiment for use in interventional radiology, the catheter portion 12 is a 3.5 French or smaller diameter catheter with an internal lumen of 0.026 to 0.010 inches. As seen in FIGS. 1a, 2b, 3a, and 8a, the catheter portion 12 can be viewed as having a proximal segment 13 near the hub 11, followed by a middle segment 14, and a distal segment 15 which terminates in a tip 16. The over all length of the catheter portion 12 will typically measure 150 cm, but it can be made in varying sizes between 60 cm and 175 cm in length. The catheter portion 12 is made of any of a number of plastic materials, including polyethylene, polyurethane, may be coated internally or externally with a hydrophilic coating, and may contain metal braiding inherent to its walls. Preferably, the distal segment 15 of the catheter will include a radio-opaque marker band 27 (FIG. 3a) near the tip 16 so that the radiologist can accurately track the movement and position of the catheter tip 16.

In accordance with one of the novel features of the microcatheter 10, a parachute structure 20 is attached to the distal segment 15 of the catheter 12 by one or more distal control strings 21 and one or more proximal control strings 22. The strings 21, 22 can be strings, wires, or cables made of a flexible, high-tensile strength biocompatible material. They may be radioopaque. The parachute structure 20 will preferably have either a rectangular shape (FIGS. 5a–c) or a triangular shape (FIG. 6a–c).

The hub portion 11 of the microcatheter 10 remains outside the body when the microcatheter 10 is used. The hub 11 is also made of plastic and has an internal geometry in the shape of a funnel such that the input side of the hub 11 is easily connected to a standard 2 or 3-way stopcock (not shown). The output side of the hub 11 (the narrow end of the funnel) connects to the small internal lumen of the catheter portion 12.

Figure 2A:
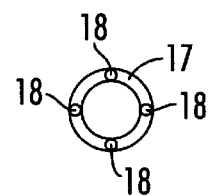
FIG. 2a is a cross-sectional end view of a middle segment of the microcatheter showing the string channels through the walls of the microcatheter.
Figure 2B:
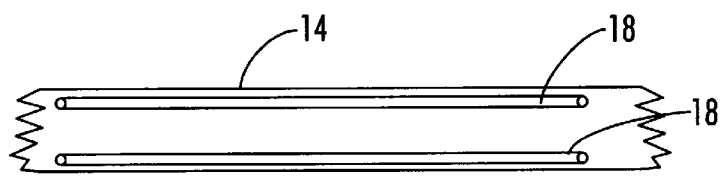
FIG. 2b is a cutaway side view of the microcatheter middle segment of FIG. 2a, with the control strings arranged in a linear or straight pattern within the catheter wall.
Figure 2C:
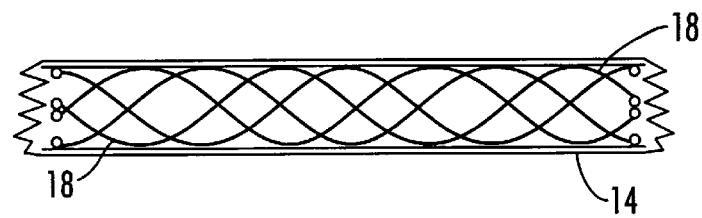
FIG. 2c is a cutaway side view of a middle section of the microcatheter segment of FIG. 2a, but with the strings arranged in a spiral pattern within the catheter wall.

Looking at FIG. 2a, the cylindrical wall 17 of the catheter 12 is manufactured so that four small diameter string channels 18 are formed within the wall 17 and traverse the length of the catheter 12 either in a straight (FIG. 2b) or spiral (FIG. 2c) configuration. The string channels 18 must be large enough to slidably accommodate the distal and proximal control strings 21, 22 and small enough so that they do not significantly alter the strength, trackability, or stiffness of the inherent microcatheter. When the triangular form of the parachute 20 is used, only 3 straight or spiral channels 18 are necessary.

Figure 1B:
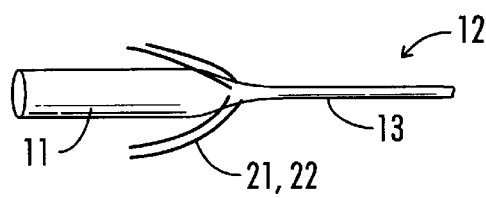
FIG. 1b is a side view of a second embodiment of the microcatheter in which the control strings are incorporated into the proximal portion of the hub proper.
Figure 3A:
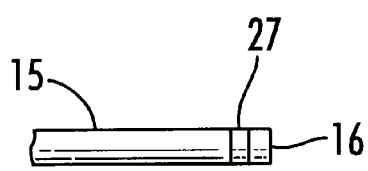
FIG. 3a is a side view of the distal segment of the microcatheter and tip, showing a radio-opaque marker band located proximal to the tip orifice FIG. 3b a cross-sectional end view of the tip of the microcatheter, showing the distal control strings exiting from string channels arranged in opposed positions at points near the transverse midline of the catheter wall.
Figure 3B:
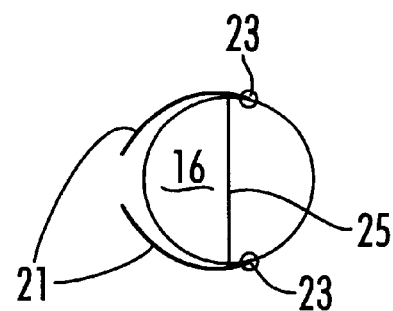
FIG. 3c is a cross-sectional of the distal segment of the microcatheter showing the proximal control strings exiting from string channels arranged in opposed positions at points near the transverse midline of the catheter wall.
FIG. 3d is a plan view of the microcatheter of FIGS. 3a. b. and c showing the parachute in its non-deployed position adjacent the exterior wall of the microcatheter, with the distal control strings coursing to the opposite side of the microcatheter tip and towards their respective channel apertures, and the proximal control strings coursing to the proximal string channel apertures.

Within each of the four channels 18 are the proximal and distal control strings 21, 22. The control strings 21, 22 enter their corresponding channels 18 through openings in the catheter wall 17 near or through the base of the hub 11 (FIGS. 1a and 1b.) The strings 21, 22 then extend through their corresponding channels 18 the length of the catheter 12 to the distal segment 15 of the catheter. The distal control strings 21 exit their corresponding channels 18 through distal string apertures 23 through the catheter wall 17, close to the tip 16. As seen on FIG. 3b, the distal string apertures 23 are formed at opposed positions that are near but slightly separated from the transverse midline 25 of the catheter tip 16. As best seen on FIGS. 3c and 3d, the proximal control strings 22 exit from their channels 18 through proximal string apertures 24 that are positioned away from the distal string apertures 23. The proximal string apertures 24 are located through the catheter wall 17 in positions opposite of the distal string apertures 23, separated slightly away from the midline 25. Thus, the linear distance between the respective distal and proximal string apertures 23, 24 is slightly less than the diameter of the catheter 12.

Figure 5A:
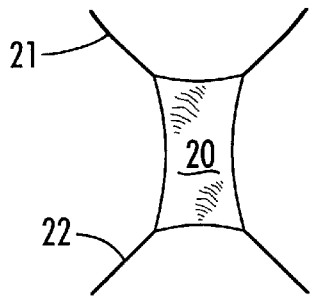
FIG. 5a is a plan view of a first embodiment of the parachute structure of the microcatheter of the present invention, showing each of the distal and proximal strings attached to a corresponding corner of a rectangular parachute.
Figure 5B:
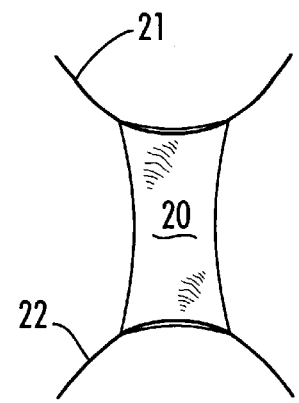
FIG. 5b is a plan view of a second embodiment of the parachute structure of the microcatheter of the present invention in which two control strings have been used, one distal string exiting and returning through the distal channel apertures, and the proximal string exiting and returning through the proximal channel apertures, each of the strings coursing through the width end margins of a rectangular parachute, respectively.
Figure 5C:
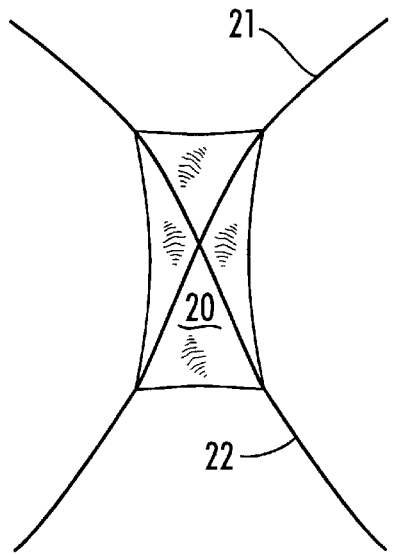
FIG. 5c is a plan view of a third embodiment of the parachute structure of the microcatheter of the present invention, illustrating a cross configuration of two control strings used with a rectangular parachute, with each control string coursing from a distal string channel aperture to an opposite proximal string channel aperture.
Figure 6A:
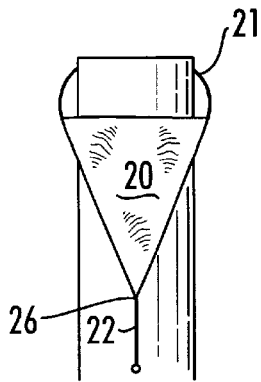
FIG. 6a is plan view of the distal segment of the microcatheter and tip, with a triangular shaped parachute in its non-deployed position proximate the exterior side wall of the distal and tip segment of the microcatheter.
Figure 6B:
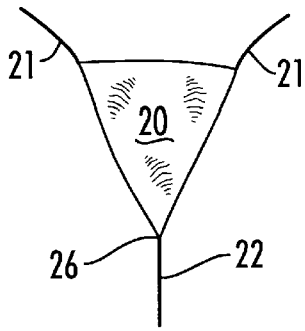
FIG. 6b is a first embodiment of a triangular shaped parachute structure with a single proximal control string and two distal control strings attached to corresponding corners of the parachute.
Figure 6C:
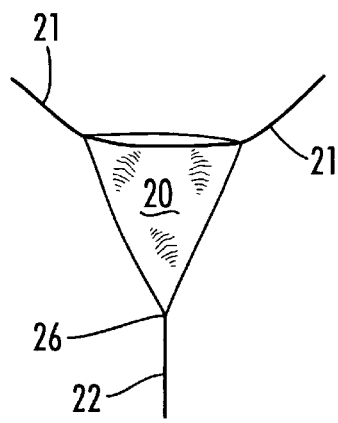
FIG. 6c is a second embodiment of a triangular shaped parachute structure with a single proximal string attached to one corner of the parachute, and a single distal string attached along the distal margin of the parachute.
Figure 7C:
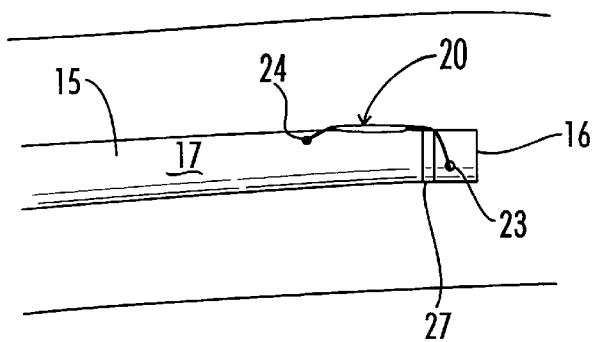
Figure 7B:
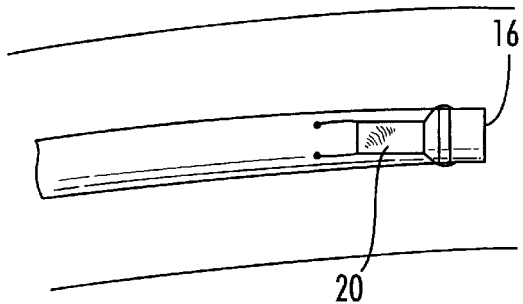
Figure 7A:
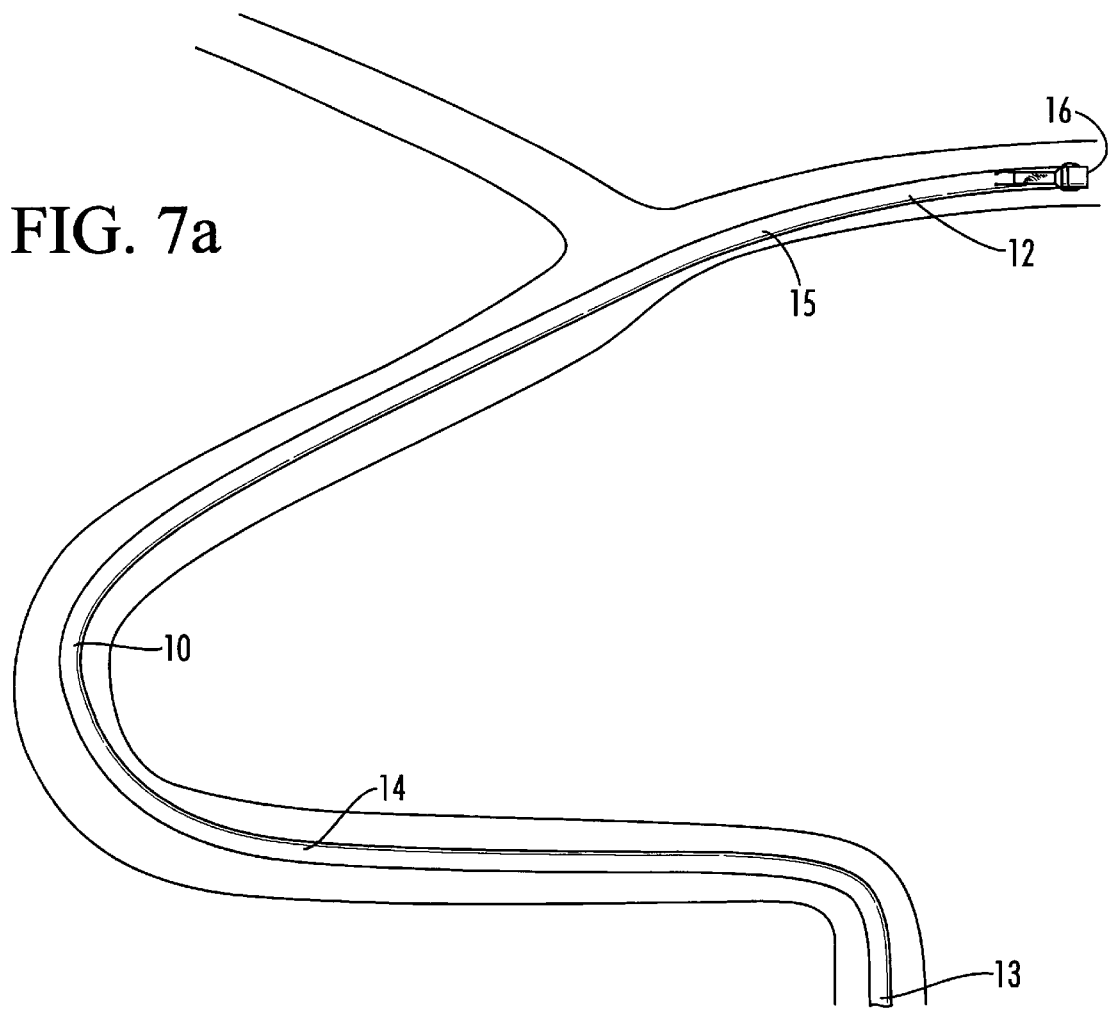
FIG. 7a is a plan view of the microcatheter of the present invention positioned inside a vascular structure with the parachute in its non-deployed or parked position.

In the preferred embodiments of FIGS. 5a–c, the distal and proximal control strings 21, 22 are attached to the corners of a rectangular parachute 20 made of a radio-opaque, biocompatible material, such as silicon, that retains its shape when exposed to blood at 37° centigrade. Alternatively, the parachute 20 may be triangular in shape (FIGS. 6a–c) with the proximal corner 26 aligned with the long axis of the catheter 12 when the parachute 20 is in a parked or non-deployed position as shown on FIG. 7.

The control strings 21, 22 may be attached to the parachute 20 in any of a number of configurations, some of which are illustrated in FIGS. 5a–c and 6a–c. For example, as seen in FIG. 5a, the four control strings 21, 22 can be attached to the four corners of the parachute 20. In FIG. 5b, two control strings are actually one string, with a proximal string 22 attached along the proximal marginal edge of the parachute 20, and the distal control string 21 attached along the more distal marginal edge of the parachute 20. Or, as illustrated in FIG. 5c, the distal and proximal control strings 21, 22 can be oriented in a criss-cross configuration, with the distal string 21 extending from a distal corner of the parachute 20 and, embedded into the parachute 20, connected to the diagonally opposite proximate corner of the parachute 20. The proximal string 22 is then attached in an opposite diagonal configuration.

When employing a triangular shaped parachute 20 as in FIGS. 6a–c, the two distal strings 21 are attached to the distal corners of the parachute 20 (FIG. 6b). Alternatively, a single distal string 21 can be attached along the distal margin of the parachute, as seen in FIG. 6c. The control strings 21, 22 must be attached to the parachute 20 in a conventional manner such that there would be no possibility of tearing at the junction point.

Figure 3D:
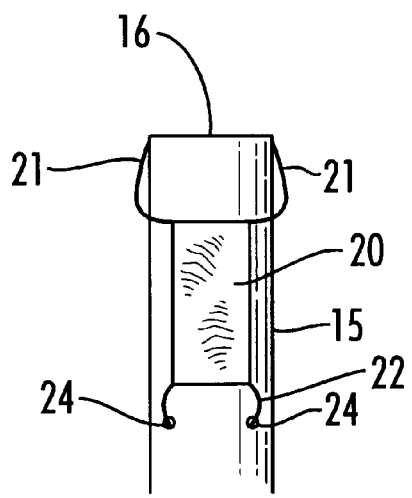
Figure 3C:
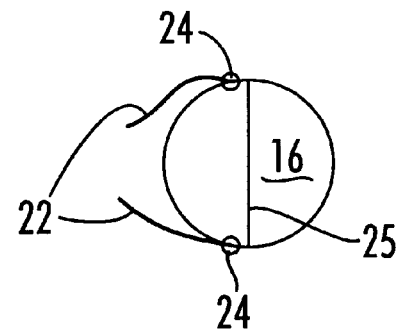
Figure 4:
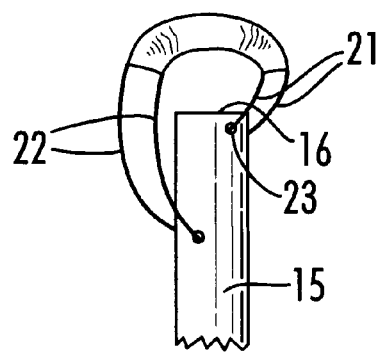
FIG. 4 is a plan view of the distal segment of the microcatheter and tip with the parachute in a deployed position located distally of or above the microcatheter tip, attached to two distal control strings and two proximal control strings.

As seen on FIG. 3d and FIG. 8b, the proximal width of the deployed parachute 20 should be slightly less than the width of the catheter 12. The length of the parachute 20 is approximately 3 mm.

When beginning use of the parachute microcatheter 10, the non-deployed parachute 20 will be "parked" near the exterior surface of wall 17 at the distal segment 15 so that the catheter 10 and parachute 20 combination will have a low profile. This is done by having the radiologist manipulate the hub end of the control strings 21, 22 (FIGS. 1a–b). The catheter 12 and parachute 20 will then be advanced through a "Y" connector connected to a guiding catheter (not shown), exiting the vessel in which the tip of the guiding catheter resides. Once the catheter 12 is recognized to have exited the guiding catheter and is identified by the radio-opaque marker band 27 in the tip of the microcatheter, the control strings 21, 22 are then advanced distally by the radiologist so that the parachute 20 is deployed, as shown on FIG. 8. The parachute 20 is opened by the flowing blood and/or injection of saline or contrast through the tip 16 of the catheter 12. Once the parachute 20 is opened, this will pull the catheter 12 into the cerebral vasculature. Movement of the catheter can be directed to the appropriate vasculature by manipulation of the control strings 21, 22 just as a target skydiver will control his or her parachute. Alternatively, if a high-flow situation is not present, the parachute 20 can be used to access the largest intracranial vessels then can be withdrawn to resume its parked position flush with the tip 16. Then a guide wire can be employed through the lumen of the catheter 12. Because of the location of the control string apertures 23, 24 the strings will not obstruct the tip 16 and will assume a position along the outer wall 17. When the procedure is complete, the radiologist will then manipulate the control strings 21, 22 in a proximal direction, causing the parachute to once again assume the parked position. The catheter 12 can then be withdrawn.

The embodiments of the microcatheter described herein are shown with three or four control strings. However, more control strings could be used without departing from the scope of the invention.

Thus, although there have been described particular embodiments of the present invention of a new and useful "Microcatheter with Auxiliary Parachute Guide Structure", it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. A catheter device comprising:
   a. a catheter having a cylindrical wall surrounding a lumen;
   b. a flexible parachute structure connected to a distal segment of the catheter by a plurality of control strings;
   c. string channels formed in the catheter wall to slidably receive the control strings, the string channels and control strings extending from the distal segment of the catheter to a proximal segment of the catheter; and
   d. whereby manipulation of the control strings through the string channels from the proximal end of the catheter causes the parachute to assume a non-deployed position proximate the catheter wall during removal of the device and a deployed position away from the catheter wall as an aid in guiding the device through a flowing liquid toward a target area.

2. The device of claim 1 wherein the parachute structure has two distal corners and a proximal corner to define a parachute having a triangular shape, and the control strings comprise two distal control strings attached to respective distal corners and a proximal control string attached to the proximal corner.

3. The device of claim 2 wherein the distal control strings each enter one of the string channels through respective distal apertures which pass through the catheter wall at the distal segment of the catheter and the proximal control string enters another of the string channels through a proximal aperture which passes through the catheter wall at the distal segment of the catheter.

4. The device of claim 3 wherein the distal apertures are arranged in opposed positions proximate a transverse midline through the catheter such that the distal apertures are separated by a distance which is slightly smaller than a diameter of the catheter, and wherein the proximal aperture is arranged in a more proximal position on the distal segment of the catheter on an opposite side of the midline.

5. The device of claim 1 wherein the string channels are arranged in a braid pattern within the catheter wall.

6. The device of claim 1 wherein the parachute structure has two distal corners and two proximal corners to define a parachute having a rectangular shape and the control strings comprise two distal control strings attached to respective distal corners and two proximal control strings attached to respective proximal corners.

7. The device of claim 6 wherein the distal control strings each enter one of the string channels through respective distal apertures which pass through the catheter wall at the distal segment of the catheter and the proximal control strings each enter another of the string channels through respective proximal apertures which pass through the catheter wall at the distal segment of the catheter.

8. The device of claim 7 wherein the distal apertures are arranged in opposed positions proximate a transverse midline through the catheter such that the distal apertures are separated by a distance which is slightly smaller than a diameter of the catheter, and wherein the proximal apertures are each arranged in a more proximal position on the distal segment of the catheter on an opposite side of the midline such that the proximal apertures are separated by a distance which is slightly smaller than the diameter of the catheter.

9. The device of claim 8 wherein the distal control strings each enter one of the string channels through respective distal apertures which pass through the catheter wall at the distal segment of the catheter and the proximal control string enters another of the string channels through a proximal aperture which passes through the catheter wall at the distal segment of the catheter.

10. The device of claim 6 wherein the string channels are arranged in a braid pattern within the catheter wall.

11. A catheter comprising:
 a. a catheter wall surrounding a lumen;
 b. a plurality of control strings that enter the catheter wall at a proximal segment of the microcatheter and extend through string channels in the catheter wall and then exit the string channels at apertures formed in the wall at a distal segment of the microcatheter;
 c. a flexible parachute structure connected to each of the control strings at the distal segment of the microcatheter such that a user of the microcatheter can move the parachute structure from a parked position adjacent the catheter wall into a deployed position and direct movement of the microcatheter within a flowing liquid by manipulating the control strings from the proximal segment of microcatheter such that the flowing liquid acts against the parachute structure to aid in advancing the catheter toward a target area; and
 d. the parachute structure is movable by the control strings from the deployed position back to the parked position for removal of the catheter.

12. A method of directing a catheter through vasculature in a patient toward a target area comprising the steps of:
 a. providing the catheter with a flexible auxiliary guiding structure near a distal segment of the catheter which can be manipulated using control strings which extend from the distal segment of the catheter back through the catheter to a control position outside the patient;
 b. retracting the guiding structure into a non-deployed position proximate the catheter such that a low profile is presented;
 c. advancing the microcatheter toward the target;
 d. deploying the guiding structure into a position such that a liquid flowing toward a tip of the catheter will flow against the guiding structure;
 e. manipulating the guiding structure using the control strings to direct a further advance of the catheter toward the target area;
 f. retracting the guiding structure back into the non-deployed position; and
 g. withdrawing the catheter from the patient.

13. A catheter device adapted for manipulation through blood flowing toward a target area in a patient comprising:
 a. a catheter having a lumen enclosed by a catheter wall, a proximal end, and a distal end;
 b. an auxiliary guiding structure attached by control strings to the distal end of the catheter;
 c. the control strings extending back toward the proximal end of the catheter through string channels connected to the catheter wall; and
 d. the auxiliary guiding structure comprising a flexible material having a shape whereby manipulation of the control strings at the proximal end of the catheter can cause the auxiliary guiding structure to deploy from a low profile position proximate the catheter wall during insertion of the device into the patient, to an extended position such that the auxiliary guiding structure uses the flowing blood to assist in advancing the distal end of the catheter towards the target area, and then again to the low profile position for removal of the device from the patient.

14. The device of claim 13 wherein the string channels are formed inside the catheter wall.

* * * * *